(12) United States Patent
Higuchi et al.

(10) Patent No.: US 8,039,215 B2
(45) Date of Patent: Oct. 18, 2011

(54) MULTIPLEX QUANTITATIVE NUCLEIC ACID AMPLIFICATION AND MELTING ASSAY

(75) Inventors: Russell Higuchi, Alameda, CA (US); Cherie Holcomb, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 236 days.

(21) Appl. No.: 12/400,966

(22) Filed: Mar. 10, 2009

(65) Prior Publication Data

US 2010/0233686 A1    Sep. 16, 2010

(51) Int. Cl.
*C12Q 1/68*    (2006.01)
*C12P 19/34*    (2006.01)
(52) U.S. Cl. .................... 435/6.12; 435/91.2
(58) Field of Classification Search ............. 435/6, 91.2
See application file for complete search history.

(56) References Cited

U.S. PATENT DOCUMENTS

| | | | |
|---|---|---|---|
| 6,140,054 A | 10/2000 | Wittwer et al. | |
| 6,245,514 B1 | 6/2001 | Wittwer | |
| 6,472,156 B1 | 10/2002 | Wittwer et al. | |
| 6,569,627 B2 | 5/2003 | Wittwer et al. | |
| 7,019,129 B1 * | 3/2006 | Cook et al. ............ | 536/26.6 |
| 2004/0175752 A1 | 9/2004 | Schaffer et al. | |
| 2005/0053950 A1 * | 3/2005 | Zudaire Ubani et al. ......... | 435/6 |
| 2006/0177841 A1 | 8/2006 | Wangh et al. | |

FOREIGN PATENT DOCUMENTS

| | | |
|---|---|---|
| EP | 1288314 A2 | 3/2003 |
| EP | 1288314 A3 | 2/2004 |
| EP | 1288314 B1 | 8/2006 |
| EP | 10002350 | 7/2010 |
| WO | 0018965 A1 | 4/2000 |
| WO | 2004074447 A2 | 9/2004 |
| WO | 2004074447 A3 | 9/2004 |
| WO | 2009042728 A1 | 4/2009 |
| WO | 2009135832 A1 | 11/2009 |

OTHER PUBLICATIONS

Bell, Andrew S., et al., 2002, "Real-time quantitative PCR in parasitology", Trends in Parasitology, 18(8):337-342.
Castro, Maria E., et al., 2008, "PPP1CA contributes to the senescence program induced by oncogenic Ras", Carcinogenesis, 29(3):491-499.
De Silva, Deepika, et al., 1998, "Rapid Genotyping and Quantification on the LightCycler (TM) with Hybridization Probes", Biochemica, 2:12-15.
Muller, Stefan, et al., 2001, "Sumo, Ubiquitin's Mysterious Cousin", Nature Reviews/Molecular Cell Biology, 2:2002-210.
Ririe, Kirk M., et al., 1997, "Product Differentiation by Analysis of DNA Melting Curves during the Polymerase Chain Reaction", Analytical Biochemistry, 245:154-160.
Sparano, Joseph A., et al., 2008, "Development of the 21-Gene Assay and Its Application in Clinical Practice and Clinical Trials", Journal of Clinical Oncology, 26(6):721-728.
Wittwer, Carl T., et al., 2001, "Real-Time Multiplex PCR Assays", Methods, 25:430-442.
Yeh, Edward T. H., et al., 2000, "Ubiquitin-like proteins: new wines in new bottles", Gene, 248:1-14.
Longo, Mary C., et al., 1990, "Use of uracil DNA glycosylase to control carry-over contamination in polymerase chain reaction", Gene, 93(1):125-128.
Szilvasi, Aniko, et al., 2005, "Asymmetric PCR increases efficiency of melting peak analysis on the LightCycler", Clinical Biochemistry, 38(8):727-730.
Zhang, Xiuling, et al., 2004, "Development of a Real-Time Polymerase Chain Reaction-Based Method for the Measurement of Relative Allelic Expression and Identification of CYP2A13 Alleles with Decreased Expression in Human Lung", 311(1):373-381.

* cited by examiner

*Primary Examiner* — Kenneth R. Horlick
(74) *Attorney, Agent, or Firm* — Charles M. Doyle; Olga Kay (57) ABSTRACT

The invention is a single-tube multiplex assay, capable of simultaneously amplifying, detecting and quantifying multiple nucleic acid targets, using multiple hybridization probes, labeled with the same fluorescent reporter label, but each having a distinct melting temperature. The assay can be further multiplexed with the use of multiple sets of hybridization probes, each set labeled with a separate fluorescent reporter label.

8 Claims, 3 Drawing Sheets

MULTIPLEX QUANTITATIVE NUCLEIC ACID AMPLIFICATION AND MELTING ASSAY

FIELD OF THE INVENTION

The invention relates generally to in vitro amplification, detection and quantification of nucleic acids. Specifically, the invention relates to a single-tube multiplex assay, capable of simultaneously amplifying, detecting and quantifying multiple nucleic acid targets, using multiple hybridization probes, labeled with the same fluorescent reporter label. The assay can be further multiplexed with the use of several fluorescent reporters.

BACKGROUND OF THE INVENTION

The polymerase chain reaction (PCR) has become a ubiquitous tool of biomedical research, disease monitoring and diagnostics. Amplification of nucleic acid sequences by PCR is described in U.S. Pat. Nos. 4,683,195, 4,683,202, and 4,965,188. PCR is now well known in the art and has been described extensively in the scientific literature. See *PCR Applications*, ((1999) Innis et al., eds., Academic Press, San Diego), *PCR Strategies*, ((1995) Innis et al., eds., Academic Press, San Diego); *PCR Protocols*, ((1990) Innis et al., eds., Academic Press, San Diego), and *PCR Technology*, ((1989) Erlich, ed., Stockton Press, New York). A "real-time" PCR assay is able to simultaneously amplify and detect and quantify the starting amount of the target sequence. The basic TaqMan real-time PCR assay using nuclease activity of the DNA polymerase is described in Holland et al., (1991) *Proc. Natl. Acad. Sci.* 88:7276-7280 and U.S. Pat. No. 5,210,015. The real-time PCR without the nuclease activity (a nuclease-free assay) has been described in a U.S. application Ser. No. 12/330,694 filed on Dec. 9, 2008. The use of fluorescent probes in real-time PCR is described in U.S. Pat. No. 5,538,848.

A typical real-time PCR protocol involves the use of a labeled probe, specific for each target sequence. The probe is preferably labeled with one or more fluorescent moieties, which emit light of a detectable wavelength. Upon hybridizing to the target sequence or its amplicon, the probe exhibits a detectable change in fluorescent emission.

The major challenge of the real-time assay however remains the ability to analyze numerous targets in a single tube. In virtually every field of medicine and diagnostics, the number of loci of interest increases rapidly. For example, multiple loci must be analyzed in forensic DNA profiling, pathogenic microorganism detection, multi-locus genetic disease screening and multi-gene expression studies, to name a few.

With the current methods, the ability to multiplex an assay is limited by the detection instruments. Specifically, the use of multiple probes in the same reaction requires the use of distinct fluorescent labels. To simultaneously detect multiple probes, an instrument must be able to discriminate among the light signals emitted by each probe. The current technology does not permit detection of more than four separate wavelengths in the same reaction vessel. For example, Bell et al. ("*Real-time quantitative PCR in parasitology*," Trends in Parasitol. (2002) 18(8):337-342.) have recently surveyed available real-time quantitative PCR thermal cyclers and reported that none have more than four optical detection channels. Therefore, using one uniquely-labeled probe per target, no more than four separate targets can be detected in the same vessel. In practice, at least one target is usually a control nucleic acid. Accordingly, in practice, no more than three experimental targets can be detected in the same tube. Since the optical hardware may offer at most, a small incremental improvement, the ability to multiplex an assay will not keep pace with the clinical needs, unless radical changes in the amplification and detection strategy are made.

An additional ability to multiplex a real-time amplification reaction is provided by a post-PCR melting assay. See U.S. patent application Ser. No. 11/474,071, filed on Jun. 23, 2006. In a melting assay, the amplified nucleic acid is identified by its unique melting profile. A melting assay involves determining the melting temperature (melting point) of a double-stranded target, or a duplex between the labeled probe and the target. As described in U.S. Pat. No. 5,871,908, to determine melting temperature using a fluorescently labeled probe, a duplex between the target nucleic acid and the probe is gradually heated (or cooled) in a controlled temperature program. The dissociation of the duplex changes the distance between interacting fluorophores or fluorophore and quencher. The interacting fluorophores may be conjugated to separate probe molecules, as described in U.S. Pat. No. 6,174,670. Alternatively, one fluorophore may be conjugated to a probe, while the other fluorophore may be intercalated into a nucleic acid duplex, as described in U.S. Pat. No. 5,871,908. As yet another alternative, the fluorophores may be conjugated to a single probe oligonucleotide. Upon the melting of the duplex, the fluorescence is quenched as the fluorophore to the quencher are brought together in the now single-stranded probe.

The melting of the nucleic acid duplex is monitored by measuring the associated change in fluorescence. The change in fluorescence may be represented on a graph referred to as "melting profile." Because different probe-target duplexes may be designed to melt (or reanneal) at different temperatures, each probe will generate a unique melting profile. Properly designed probes would have melting temperatures that are clearly distinguishable from those of the other probes in the same assay. Many existing software tools enable one to design probes for a same-tube multiplex assay with these goals in mind. For example, Visual OMP™ software (DNA Software, Inc., Ann Arbor, Mich.) enables one to determine melting temperatures of nucleic acid duplexes under various reaction conditions.

The method of multiplex PCR using color detection and subsequent post-amplification melting assay is described in U.S. Pat. No. 6,472,156. The number of targets detectable by such a method is a product of the number of detectable wavelengths and the number of distinguishable melting profiles. Therefore adding a melting assay to color detection was a step forward in the ability to detect multiple targets.

The post-amplification melting assay is most commonly used for qualitative purposes, i.e. to identify target nucleic acids, see U.S. Pat. Nos. 6,174,670, 6,427,156 and 5,871,908. It is known to obtain a melting peak by differentiating the melting curve function. Ririe et al. ("*Product differentiation by analysis of DNA melting curves during the polymerase chain reaction*," (1997) Anal. Biochem. 245:154-160) observed that differentiation helps resolve melting curves generated by mixtures of products. After differentiation, the melting peaks generated by each component of the mixture become easily distinguishable. It was also previously known that the post-amplification melting signal, i.e. melting peak, is higher in proportion to the amount of the nucleic acid in the sample. For example, U.S. Pat. No. 6,245,514 teaches a post-amplification melt assay using a duplex-intercalating dye, to generate a derivative melting peak, and then, using proprietary software, to integrate the peak. The integration provides information about the efficiency of amplification and relative amount of the amplified nucleic acid.

In practice, it would be desirable to move beyond a qualitative assay and be able to quantify multiple targets in the same sample. See e.g. Sparano et al. "*Development of the 21-gene assay and its application in clinical practice and clinical trials*," J. Clin. Oncol. (2008) 26(5):721-728. The ability to quantify the amount of target is useful in clinical applications, such as determination of viral load in a patient's serum, measuring the level of expression of a gene in response to drug therapy or determining the molecular signature of a tumor to predict its response to therapy.

In a real-time PCR assay, the signal generated by the labeled probe is proportional to the amount of input target nucleic acid. The greater the input, the earlier the fluorescence signal crosses a predetermined threshold value ($C_t$). Therefore one can determine relative or absolute amounts of the target nucleic acid by comparing the samples to each other or to a control sample with known amount of nucleic acid. However, the existing methods are limited in their ability to simultaneously quantify multiple targets. As with the qualitative detection of multiple targets, the limiting factor is the optical detector. As explained above, state-of-the-art optical technology is not able to obtain distinct signals from more than four separate fluorescently labeled probes in the same tube. The technology now in development promises detection of no more than six separate labels. Therefore a radically different experimental approach is needed to permit both amplification, detection and quantification of numerous nucleic acid targets during real-time PCR.

SUMMARY OF THE INVENTION

The present invention is a method for amplification, detection and quantification of one or more target nucleic acids in a single sample container comprising the steps of contacting a sample, suspected of containing one or more target nucleic acids, with at least one set of oligonucleotides, each oligonucleotide within the set labeled with the same one or more reporter moieties, wherein each said labeled oligonucleotide is sufficiently complementary to at least a subsequence of at least one target nucleic acid; is capable of binding to the corresponding target nucleic acid with a melting temperature distinct from the melting temperatures of the other labeled oligonucleotides within the same set; amplifying the target nucleic acids in the sample in an amplification reaction that includes a temperature change interval, wherein the one or more labeled oligonucleotides dissociate from the hybrids with the corresponding target nucleic acids; detecting light emission from said reporter moiety over at least a portion of said temperature change interval; and plotting the first derivative of said light emission over at least said portion of the temperature change interval; determining the maximum value of said derivative; repeating the above mentioned steps multiple times; and plotting the maximum values of said derivative against the number or repetitions, and determining the number of repetitions at which the predetermined threshold value of said determined maximum value of the derivative is reached, thus quantifying the relative amount of said target nucleic acid.

DETAILED DESCRIPTION OF THE INVENTION

Definitions

The following definitions apply to the terms used throughout the application.

An "asymmetric PCR" is a PCR wherein the amounts of two amplification primers are unequal. The primer present at a higher amount is referred to as the "excess primer" and the primer present at a lower amount is referred to as the "limiting primer." The strand resulting from extension of the excess primer is accumulated in excess and is called "the excess strand." The other strand, resulting from extension of the limiting primer, is accumulated in smaller amounts and is called "the limiting strand."

A "chromophore" is a compound or a moiety attached for example, to a nucleic acid, which is capable of selective light absorption resulting in coloration. A chromophore may or may not emit the light radiation when excited.

A "fluorescent dye" or a "fluorophore" is a compound or a moiety attached for example, to a nucleic acid, which is capable of emitting light radiation when excited by a light of a suitable wavelength. Typical fluorescent dyes include rhodamine dyes, cyanine dyes, fluorescein dyes and BODIPY® dyes. A fluorophore is a fluorescent chromophore.

"FRET" or "fluorescent resonance energy transfer" or "Foerster resonance energy transfer" is a transfer of energy between at least two chromophores, a donor chromophore and an acceptor chromophore (referred to as a quencher). The donor typically transfers the energy to the acceptor when the donor is excited by light radiation with a suitable wavelength. The acceptor typically re-emits the transferred energy in the form of light radiation with a different wavelength. When the acceptor is a "dark" quencher, it dissipates the transferred energy in a form other than light. Whether a particular fluorophore acts as a donor or an acceptor depends on the properties of the other member of the FRET pair. Commonly used donor-acceptor pairs include the FAM-TAMRA pair. Commonly used quenchers are DABCYL and TAMRA. Commonly used dark quenchers are BlackHole Quenchers™ (BHQ), Biosearch Technologies, Inc. (Novato, Calif.), Iowa Black™, Integrated DNA Tech., Inc. (Coralville, Iowa), BlackBerry™ Quencher 650 (BBQ-650), Berry & Assoc., (Dexter, Mich.). Commonly used donor-quencher pairs include the FAM-BHQ pair.

A "growth curve" in the context of a nucleic acid amplification assay is a graph of a function, where an independent variable is the number of amplification cycles and a dependent variable is an amplification-dependent measurable parameter measured at each cycle of amplification. Typically, the amplification-dependent measurable parameter is the amount of fluorescence emitted by the probe upon hybridization, or upon the hydrolysis of the probe by the nuclease activity of the nucleic acid polymerase, see Holland et al., (1991) *Proc. Natl. Acad. Sci.* 88:7276-7280 and U.S. Pat. No.

5,210,015. In a typical polymerase chain reaction, a growth curve comprises a segment of exponential growth followed by a plateau. A growth curve is typically characterized by a "cycles to threshold" value or "$C_t$" value, which is a number of cycles where a predetermined magnitude of the measurable parameter is achieved. A lower $C_t$ value represents more rapid completion of amplification, while the higher $C_t$ value represents slower completion of amplification. Where the efficiency of amplification is similar, the lower $C_t$ value is reflective of the higher starting amount of the target nucleic acid, while the higher $C_t$ value is reflective of the lower starting amount of the target nucleic acid. Where a control nucleic acid of known concentration is used, it becomes possible to determine the absolute amount of the target nucleic acid by comparing the $C_t$ values of the target and control nucleic acids.

A "hot start" in the context of a nucleic acid amplification reaction is a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

"Hybridization" is an interaction between two usually single-stranded or at least partially single-stranded nucleic acids. Hybridization occurs as a result of base-pairing between nucleobases and involves physicochemical processes such as hydrogen bonding, solvent exclusion, base stacking and the like. Hybridization can occur between fully-complementary or partially complementary nucleic acid strands. The ability of nucleic acids to hybridize is influenced by temperature and other hybridization conditions, which can be manipulated in order for the hybridization of even partially complementary nucleic acids to occur. Hybridization of nucleic acids is well known in the art and has been extensively described in Ausubel (Eds.) *Current Protocols in Molecular Biology*, v. I, II and III (1997).

A "label" refers to a moiety attached (covalently or non-covalently), to a molecule, which moiety is capable of providing information about the molecule. Exemplary labels include fluorescent labels, radioactive labels, and mass-modifying groups.

A term "nucleic acid" refers to polymers of nucleotides (e.g., ribonucleotides and deoxyribonucleotides, both natural and non-natural) such polymers being DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. The example of non-natural bases include those described in, e.g., Seela et al. (1999) *Helv. Chim. Acta* 82:1640. Certain bases used in nucleotide analogs act as melting temperature ($T_m$) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

The term "nucleic acid polymerases" or simply "polymerases" refers to enzymes, for example, DNA polymerases, that catalyze the incorporation of nucleotides into a nucleic acid. Exemplary thermostable DNA polymerases include those from *Thermus thermophilus*, *Thermus caldophilus*, *Thermus* sp. ZO5 (see, e.g., U.S. Pat. No. 5,674,738), *Thermus aquaticus*, *Thermus flavus*, *Thermus filiformis*, *Thermus* sp. sps17, *Deinococcus radiodurans*, Hot Spring family B/clone 7, *Bacillus stearothermophilus*, *Bacillus caldotenax*, *Escherichia coli*, *Thermotoga maritima*, *Thermotoga neapolitana* and *Thermosipho africanus*. The full nucleic acid and amino acid sequences for numerous thermostable DNA polymerases are available in the public databases.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

The terms "nucleic acid polymerase substantially lacking the 5'-3' nuclease activity" or "5'-3'-nuclease-deficient enzyme", or for simplicity, "nuclease-deficient enzyme" refer to a polymerase that has 50% or less of the 5'-3' activity than Taq DNA polymerase. The methods of measuring the 5'-3' nuclease activity and conditions for measurement have been described in U.S. Pat. No. 5,466,591. The examples of polymerases lacking the 5'-3' nuclease activity include the Stoffel fragment of Taq DNA polymerase (U.S. Pat. No. 5,466,591), mutants of *Thermus africanus* DNA polymerase (U.S. Pat. No. 5,968,799), mutants of *Thermotoga maritima* DNA polymerase (U.S. Pat. Nos. 5,624,833 and 5,420,029), mutants of *Thermus* species sps17 and *Thermus* species Z05 DNA polymerases (U.S. Pat. Nos. 5,466,591 and 5,405,774). 5'-3' nuclease deficient enzymes may also be chimeras, i.e. chimeric proteins, composed of domains derived from more than one species and having mutations that eliminate the 5'-3' nuclease activity (U.S. Pat. Nos. 5,795,762 and 6,228,628).

An "oligonucleotide" refers to a short nucleic acid, typically ten or more nucleotides in length. Oligonucleotides are prepared by any suitable method known in the art, for example, direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191; or any other method known in the art.

A "primer" is an oligonucleotide, which is capable of acting as a point of initiation of extension along a complementary strand of a template nucleic acid. A primer that is at least partially complementary to a subsequence of a template nucleic acid is typically sufficient to hybridize with template nucleic acid and for extension to occur.

A "primer extension" refers to a chemical reaction where one or more nucleotides have been added to the primer.

A "probe" refers to a labeled oligonucleotide which forms a duplex structure with a sequence in the target sequence, due to at least partial complementarity of the probe and the target sequence.

A "template" or "target" refers to a nucleic acid which is to be amplified, detected and quantified. The target or template is a sequence to which a primer or a probe can hybridize.

Target nucleic acids can be derived from essentially any source, including microorganisms, complex biological mixtures, tissues, bodily fluids, sera, preserved biological samples, environmental isolates, in vitro preparations or the like. The template or target may constitute all or a portion of a nucleic acid molecule.

A "thermostable nucleic acid polymerase" or "thermostable polymerase" is a polymerase enzyme, which is relatively stable at elevated temperatures when compared, for example, to polymerases from *E. coli*. As used herein, a thermostable polymerase is suitable for use under temperature cycling conditions typical of the polymerase chain reaction ("PCR").

A "melting temperature" or "$T_m$" refers to the temperature at which one half of a population of double-stranded (duplex) nucleic acid molecules, in homoduplexes or heteroduplexes becomes dissociated into single strands. The $T_m$ of a duplex nucleic acid is affected by ionic strength and pH of the solution, as well as concentration, base composition and secondary structure of the nucleic acid itself. The $T_m$ of a duplex under given conditions can be determined experimentally or predicted with the help of commercial software, such as Visual OMP™ (DNA Software, Inc., Ann Arbor, Mich.)

A "melting assay," "melt assay," or simply "melt" is an assay in which the melting temperature ($T_m$) can be determined. In this assay, a duplex nucleic acid molecule is heated in a controlled temperature program, and the dissociation of the duplex into single strands is monitored by measuring a parameter, such as fluorescence, which changes with dissociation of the duplex. The melting data may be represented as a "melting curve," i.e. a plot of fluorescence as a function of temperature (F vs. T). The melting data may also be represented as a "melting peak," i.e. a plot of the rate of change in fluorescence over temperature interval as a function of temperature (dF/dT vs. T) or (−dF/dT vs. T), which typically has a parabolic shape. The $T_m$ of the duplex is represented on a melting peak as the temperature value (T) at the apex of the parabola (dF/dT vs. T) or (−dF/dT vs. T).

The present invention is a method of simultaneous multiplex amplification, detection and quantification of nucleic acid targets. In one aspect, the method comprises real-time PCR, combined with melt analysis. The method utilizes multiple probes labeled with the same reporter moiety, but each having a unique duplex melting temperature. Because the probes can be identified by their melting temperature, and not only by their fluorescent label, several probes in the same reaction vessel may be labeled with the same labeling moiety. The assay may be further multiplexed by using several sets of probes, each set labeled with a separate reporter moiety, up to the number of moieties distinguishable by the detection instrument.

The method of the present invention involves the generation of melt signals (melting curves) produced by each probe during amplification. The melt curve functions may be differentiated into derivative functions or "melting peaks" or "melt peaks." For each melt peak, the value of the melting peak maximum is measured. The magnitude of the melt peak maximum is proportional to the amount of the target sequence and its amplicon in the reaction mixture. When melt peak maxima are recorded during the cycles of amplification plotted against the cycle number, the series of the melt peak maximum values generates an amplification curve, similar in appearance to amplification curves generated in the traditional real-time PCR assays. Each labeled probe is able to generate a unique melting profile, distinguishable from the melting profiles of other probes. Thus each probe provides independent quantitative data for each target. Relative quantification is accomplished by determining $C_m$, the cycle at which a given melt peak reaches a predetermined threshold. An earlier (lower) $C_m$ indicates a higher input concentration of the target nucleic acid, while a later (higher) $C_m$ indicates a lower input concentration of the target nucleic acid. The predetermined threshold is set experimentally for each target nucleic acid. Typically, the threshold is a fluorescent level of a melt peak when it first becomes detectable.

Where a control nucleic acid of known concentration is amplified and detected in the same assay, it becomes possible to determine absolute input amount of the target nucleic acid by comparing the $C_m$ values of the target and control nucleic acids.

Compared to traditional multiplex real-time PCR utilizing fluorescently labeled probes, the method of the present invention has broader multiplex capabilities. A traditional real-time PCR assay is constrained by the detector's inability to separate more than a few wavelengths. In the present invention, the ability to multiplex is expanded by measuring multiple distinct melt peaks at any given wavelength.

In one aspect the present invention employs a melt assay to expand the multiplexing capability of quantitative real-time PCR. Specifically, the assay of the present invention is a multiplex version of the real-time PCR that allows simultaneous amplification, detection and quantification of multiple target nucleic acid sequences in the same tube, using multiple probes, labeled with the same fluorescent label. The probes are detected within the same wavelength channel but distinguished by their unique melting temperature.

Figure 1:
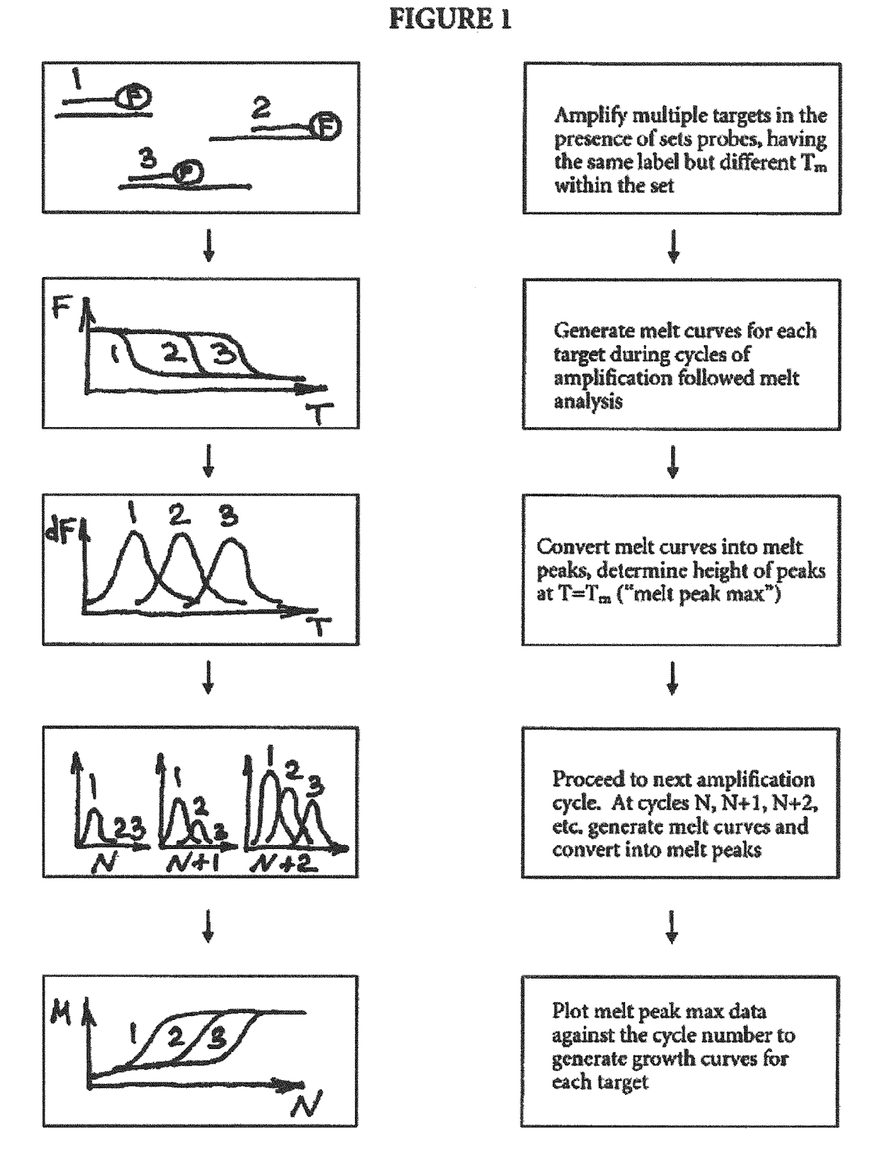
FIG. 1 is a diagram of the steps of the method of the present invention.

As shown on FIG. 1, the method of the present invention begins with amplification of several target nucleic acid sequences in the same reaction vessel. Each tube contains one or more sets of probes, each set labeled with the same fluorescent reporter. However, within the set, each probe is characterized by a unique melting temperature with its target nucleic acid. For the maximum multiplex ability, several sets of probes are present in the same reaction vessel.

After a round of amplification, the target nucleic acid may be subjected to the melt step as described below in order to generate a melt curve for each probe-target duplex. Each melt curve (fluorescence in the temperature interval, or F vs. T) is differentiated and converted into a melt peak curve in the temperature interval (dF/dT), for which a "melt peak maximum" (dF/dT at T=$T_m$) value is calculated. After repeated cycles of amplification and melting, a set of "melt peak max" values is accumulated for each target-probe complex. The melt peak max values are plotted against the number of cycles to generate a growth curve for each target nucleic acid. A growth curve, similar to typical growth curves obtained in real-time PCR assays is obtained for each target.

It some embodiments, one or more of the probes may be designed to have a melting temperature below the annealing temperature used in amplification. Such a probe would not generate a "traditional" real-time PCR growth curve. However, such a probe would be useful to generate a growth curve according to the present invention.

The target nucleic acid sequence amplified, detected and quantified by the method of the present invention can be of any length. Typically, the target nucleic acid is between 100 and 1,000 nucleotides in length. However, longer (several thousand nucleotides) and shorter (between 50 and 100 nucleotides) target sequences may also be used in some embodiments of the present invention. A target nucleic acid sequence may be contained within a larger nucleic acid molecule, isolated from a natural or laboratory-derived sample source.

While this disclosure generally discusses the invention as if there were multiple targets present in the sample, it will be appreciated that in some embodiments there is only one target sequence present in a sample. In a typical embodiment of the present invention, a "multiplex" reaction is performed where at least two and up to sixteen or more different target sequences are detected. These embodiments generally, but not always, involve the use of a separate pair of amplification primers and a separate probe for each target sequence. However, in some embodiments, the same nucleic acid, which is amplified using the same pair of primers, may be detected with more than one probe. This is advantageous where a single sequence contains several targets or loci of interest, for example, several potential mutation sites. Each probe will be able to detect and quantify the mutation at each site.

The amplification primers of the present invention are oligonucleotides at least partially complementary to at least one of the existing variants of the target sequence. The length of the primer may range between 6 and 100 nucleotides, although most primers typically range between 15 and 35 nucleotides. The methods of optimizing the primers for nucleic acid amplification have been described for example, in *PCR Protocols: A Guide to Methods and Applications*, Innis et al., eds., (1990) Academic Press. Typically, primers are synthetic oligonucleotides, composed of A, C, G and T nucleotides. However, unconventional base nucleotides, that can be incorporated into nucleic acids, can also be used in primers. For example, certain modified bases are known to increase specificity of amplification, see U.S. Pat. No. 6,001,011.

Various thermostable nucleic acid polymerases are known in the art. Any thermostable nucleic acid polymerase can be used in the method of the present invention. Sometimes it is advantageous to use a polymerase lacking the 5'-3' nuclease activity. It is sometimes desirable to use a polymerase without the proof-reading (3'-5'-exonuclease) activity. It may also sometimes be desirable to have an enzyme with a "hot start" capability, such as the reversibly modified enzymes described in U.S. Pat. Nos. 5,677,152 and 5,773,528.

The design of hybridization probes is known in the art. The same probe may serve as a hybridization probe or a melt probe or both. Whether the probe is to serve as a melt probe, a single hybridization probe or a member of a pair of hybridization probes, the design of the probe oligonucleotide is guided by the same principles, known in the art and described herein. These principles may be applied manually or with a help of software.

In some embodiments of the present invention, more than one probe may be present in the reaction mixture subjected to a melt assay. One of skill in the art would immediately recognize the design criteria applicable to melt probes useful in multiplex assays. Specifically, the probes capable of being used in the same reaction mixture should be designed to have a distinct hybrid melting temperature with their corresponding target sequences.

The probe oligonucleotides can be labeled by incorporating one or more chromophores. A single chromophore, which is a fluorophore, may be used as described in a U.S. application Ser. No. 12/330,694 filed on Dec. 9, 2008. Where two chromophores are used, one typically is a reporter chromophore and the other is a quencher. Both chromophores may be fluorophores or one of the chromophores may be a non-fluorescent quencher. Examples of suitable fluorophores include dyes of the fluorescein family (FAM, HEX, TET, JOE, NAN and ZOE), rhodamine family (Texas Red, ROX, R110, R6G and TAMRA), cyanine family (Cy2, Cy3, Cy3.5, Cy5, Cy5.5, and Cy7) coumarin family, oxazine family, thiazine family, squaranine family and other families of fluorescent dyes suitable for the labeling and detection of nucleic acids. The second chromophore may be incorporated into the same probe oligonucleotide or a separate probe oligonucleotide. Commonly used dark quenchers include BlackHole Quenchers™ (BHQ), (Biosearch Technologies, Inc., Novato, Calif.), Iowa Black™, (Integrated DNA Tech., Inc., Coralville, Iowa), and BlackBerry™ Quencher 650 (BBQ-650), (Berry & Assoc., Dexter, Mich.).

The present invention involves quantification of the target nucleic acid in a real-time PCR assay. As in the traditional real-time PCR assay, an amplification growth curve is generated for each target. The curve is generated by measuring a detectable amplification-dependent signal during each cycle of amplification. The present invention may measure a novel amplification-dependent signal, not used previously to generate growth curves. Specifically, the method of the present invention measures a melt signal, i.e. a signal generated in a melting assay in order to generate growth curves.

In the melting assay of the method of the present invention, a hybrid is formed between target DNA and one or more labeled probes. Typically, the probe or probes are labeled with one or more chromophore moieties, of which at least one chromophore is a fluorophore. The change in temperature that results in melting or formation of the template-probe hybrid is accompanied by a measurable change in fluorescence emitted by the probe upon excitation by the light of appropriate wavelength.

In some embodiments, the probe is labeled with two chromophores forming a FRET pair. In some embodiments, both chromophores are fluorophores. In other embodiments one chromophore is a non-fluorescent quencher. The chromophores forming the FRET pair may be conjugated to the same or separate probe molecules. The use of FRET probes in a melting assay has been described in U.S. Pat. No. 6,174,670 and in De Silva et al., (1998) "Rapid genotyping and quantification on the Lightcycler™ with hybridization probes," *Biochemica*, 2:12-15. In other embodiments, the probe is labeled with a single chromophore that interacts with a second chromophore either conjugated with or intercalated into the target nucleic acid. See U.S. Pat. No. 5,871,908.

According to the existing methods, a single melting assay is performed after all cycles of amplification have been completed. This technology is commonly referred to as "post-amplification melt." The present invention however, teaches to incorporate a melting assay into the cycles of PCR. This involves adding a melting step to the temperature profile of a PCR cycle. A typical melting step involves an incubation at 95° C. (to denature the double-stranded amplicons), followed by lowering the temperature to 40° C. (to allow annealing of the melt probe) and then increasing the temperature again (to melt the probe-template duplex). It was observed that the melt signal is poor in the first rounds of amplification. This phenomenon is likely due to insufficient amounts of target nucleic acid present at the early stages of amplification. It is therefore practical to incorporate melting steps into amplification cycles after a substantial number of amplification cycles have already taken place.

In a traditional real-time PCR assay with fluorescent probes, the fluorescence is detected at the annealing step of each cycle. In the present invention, the fluorescent data is acquired continuously during a selected portion of the melting step. Thus each round of melting of the probe-target duplex yields a melting curve and a melting peak. Differentiating melting curves to obtain melting peaks has been described e.g. in U.S. Pat. No. 6,472,156. For each melting peak, the melt signal is defined as the height of the melting peak or "melt peak max", when the temperature reaches the melting temperature of the duplex (T=$T_m$). The height of the melting peak is proportional to the amount of the duplex formed between the melting probe and the target amplicon and this is proportional to the amount of the target amplicon in the sample. Therefore, the cycle at which a given melt peak first reaches a predetermined threshold ($C_m$) is reflective of the initial amount of target nucleic acid. The heights of the melt peaks (melt peak max values) measured in each cycle are plotted against the cycles of amplification. As can be seen from FIGS. 2 and 3, the resulting plot resembles the traditional real-time PCR growth curve. If a control nucleic acid of known input concentration is co-amplified with the target nucleic acid, an absolute input amount of the target nucleic acid can be determined by comparing $C_m$ values measured for the target and control nucleic acids.

In some embodiments, the present invention involves asymmetric PCR. In an asymmetric PCR mixture, one of the amplification primers is present in greater amount than the other primer. The primers are referred to as "excess primer" and "limiting primer" respectively. The nucleic acid strands resulting from the extension of these primers are referred to as "excess strand" and "limiting strand" respectively. The ratio of the excess primer to the limiting primer can be selectively manipulated and be between 200:1 and 2:1, but typically about 9:1 to 5:1. Due to excess of the primer, the excess strand accumulates in a linear fashion in single-stranded form. In the present invention, the melt probes are designed to hybridize to the "excess strand," i.e. the amplicon strand that results from the extension of the excess primer, and accumulates in a single-stranded form. The excess single strand is advantageous at the later cycles of PCR. In a traditional, non-asymmetric PCR assay during later cycles, the strands of the amplicon accumulate and effectively compete with the hybridization probe for the formation of a duplex. An asymmetric PCR is designed so that the excess strand hybridizes with the probe, thus erasing the kinetic disadvantage in later cycles of PCR and allowing detection of a melting peak.

In some embodiments, it may be advantageous to use an enzyme containing 5'-3' nuclease activity. To prevent the depletion of the hybridization probe by such an enzyme, a probe concentration is chosen that ensures a sufficient amount of probe for the melt assay.

EXAMPLES

As an illustration only and not to limit the scope of the invention, the method was applied to detect the presence and amount of mRNA of human genes PPP1CA and SENP1 in the same sample. PPP1CA is a gene encoding a catalytic subunit of protein phosphatase 1-alpha and having anti-oncogenic properties. See Castro et al., "*PPP1CA contributes to the senescence program induced by oncogenic Ras*," Carcinogenesis (2008) 29(3):491-499. SENP1 is a sentrin/SUMO-specific protease, that belongs to the family of Small Ubiquitin-Like (Ubl) Modifiers (SUMO), reviewed in Muller et al., "*SUMO, ubiquitin's mysterious cousin*," Nat. Rev. Mol. Cell Biol. (2001) 2(3):202-10 and Yeh et al., "*Ubiquitin-like proteins: new wines in new bottles*," Gene (2000) 248(1-2): 1-14.

Example 1

Quantitative Amplification of Various Amounts of Targets SENP1 and PPP1CA in the Same Tube, Using Melt-Based Growth Curves In this example, the method was applied to the detection and quantification of various amounts of SENP1 and PPP1CA RNA in a tissue sample.

The asymmetric PCR was conducted with a seven-fold excess of the excess primer over the limiting primer. The detection was performed with a single hybridization probe labeled with a fluorescein dye and a BlackHole™ quencher. The primer and probe sequences are shown in Table 1. The probes were designed to hybridize to the excess strand.

TABLE 1

Primers and probes used in the examples

| Sequence ID | Function | Sequence 5'-3' |
| --- | --- | --- |
| SEQ ID NO: 1 | Forward primer for SENP1 | CAGCTTCAAATACACAATCTGAAGGATCA |
| SEQ ID NO: 2 | Reverse primer for SENP1 | TGCCTGGAAGAAAGTAGAACTGGGA |
| SEQ ID NO: 3 | Probe for SENP1 | FGACTCTGTGATTTTACTGAAAGTGAAAGATTCCCAGACTCCQp |
| SEQ ID NO: 4 | Forward primer for PPP1CA | AACCGCATATATGGTTTCTACGATGE |
| SEQ ID NO: 5 | Reverse primer for PPP1CA | CGATGAGTGCAAGAGACGCTACAE |
| SEQ ID NO: 6 | Probe for PPP1CA | FACTGTGGAAAACCTTQp |

F-cx-FAM reporter dye
Q-BHQ-2 quencher dye
E-tert-butyl-benzyl dA
p-3'-phosphate group Each 100 μL reaction contained an indicated amount of human fetal spleen RNA (between 0.2 and 2000 nanograms, as indicated on FIGS. 2 and 3) 50 mM Tricine, pH 8.3; 120 mM potassium acetate; 8% glycerol; 33.3 mM of each dATP, dGTP and dCTP, 100 mM dUTP; 40 U Z05 DNA polymerase; 100 nM Aptamer 46A; 5 U uracil-N-glycosylase (UNG); 3 mM manganese acetate; 100 nM forward (limiting) primers (SEQ ID NO: 1 and SEQ ID NO: 4); 700 nM reverse (excess) primers (SEQ ID NO: 2 and SEQ ID NO: 5); and 200 nM probes (SEQ ID NO: 3 and SEQ ID NO: 6).

The amplification and detection were performed using the Roche LightCycler™ LC480 instrument. The reactions were subjected to the following temperature profile: 50° C. for 2 min (UNG step); 95° C. for 1 min (UNG inactivation); 60° C. for 30 min (reverse transcription); followed by 44 amplification cycles of 90° C. for 15 sec (denaturation) and 61° C. for 60 sec (annealing and extension).

The melt step was incorporated after the initial 15 cycles of amplification. For cycles 16-27, the melt was performed after every second cycle. For cycles 28-39, the melt was performed after every cycle. For cycles 40-44, the melt was performed after every second cycle. The melt step commenced after the completion of the 61° C. annealing and extension step and consisted of 90° C. for 5 sec at a ramp rate of 1.2° C. per second; cooling to 40° C. at a rate of 1.8° C. per second; and heating to 90° C. at a rate of 1.8° C. per second with the fluorescent data acquired continuously, at a rate of twice per degree, reading on three channels.

For each fluorescence reading obtained in a melt step, a melting curve (function F/T) was obtained. For each melting curve, the derivative function or "melt peak" (dF/dT) was obtained and a value of the melting peak maximum was determined according to the method of the present invention. (FIG. 1). The resulting melting peak maximum values were plotted against the number of amplification cycles to yield growth curves shown on FIG. 2 (for SENP1) and FIG. 3 (for PPP1CA).

The quantitative results are shown in Table 2. The table shows the number of cycles at which a predetermined "melting threshold" ($C_m$) was reached. For SENP1, the threshold was set at 0.181. For PPPC1A, the threshold was set at 0.055. For each target, the threshold was reached earlier with the larger initial input of nucleic acid.

TABLE 2

Quantitative data (cycles to melting threshold ($C_m$) values)

| | Input RNA (ng) | | | | | |
|---|---|---|---|---|---|---|
| | 0 | 0.2 | 2 | 20 | 200 | 2000 |
| SENP1 | NC | 35.3 | 32.1 | 31.1 | 30.3 | 29.4 |
| PPPC1A | NC | 32.3 | 31.2 | 30.8 | 30.1 | 29.8 |

NC: not calculated

Figure 2:
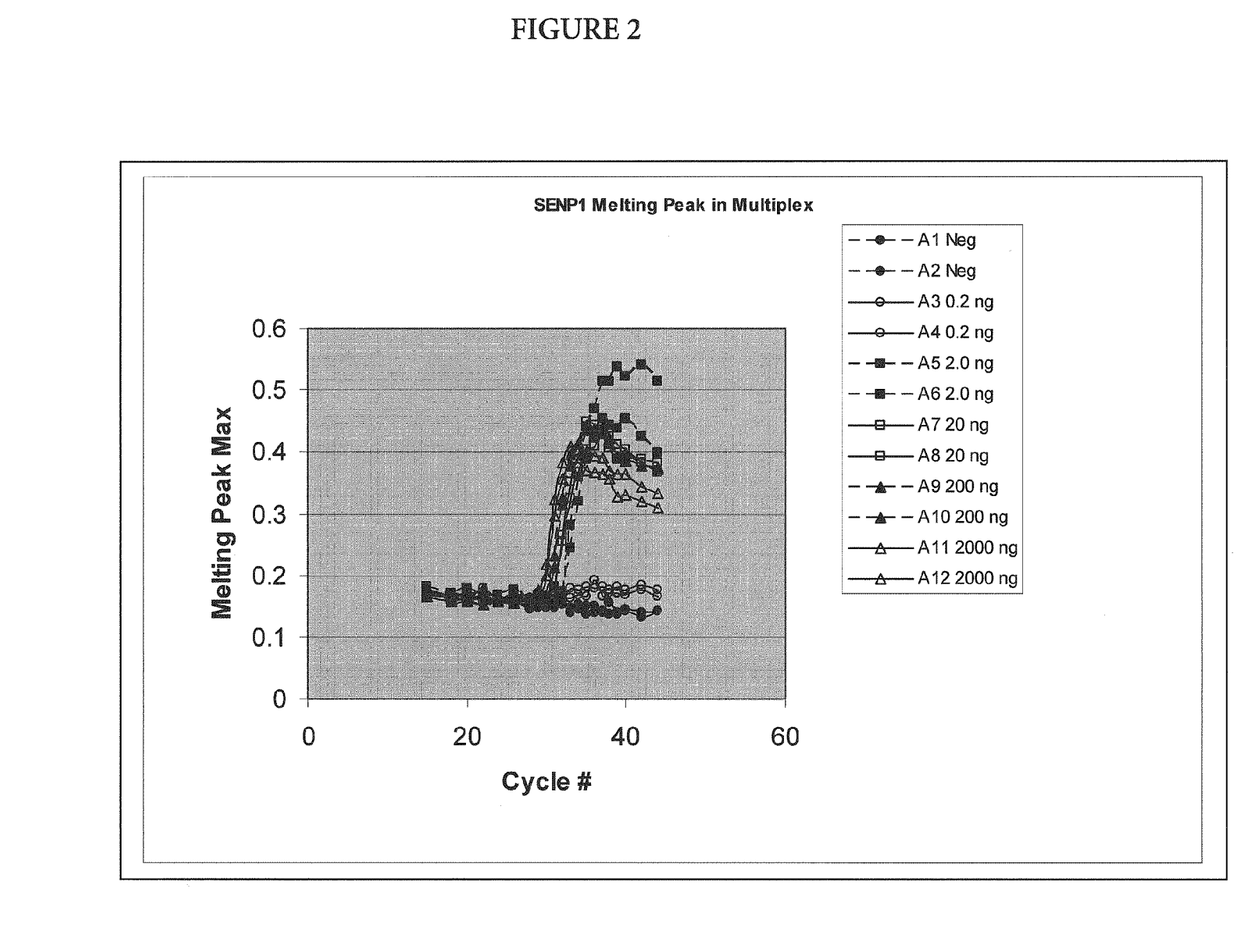
FIG. 2 shows the results of the method of the present invention as applied to the target nucleic acid sequence SENP1 and described in Example 1.
Figure 3:
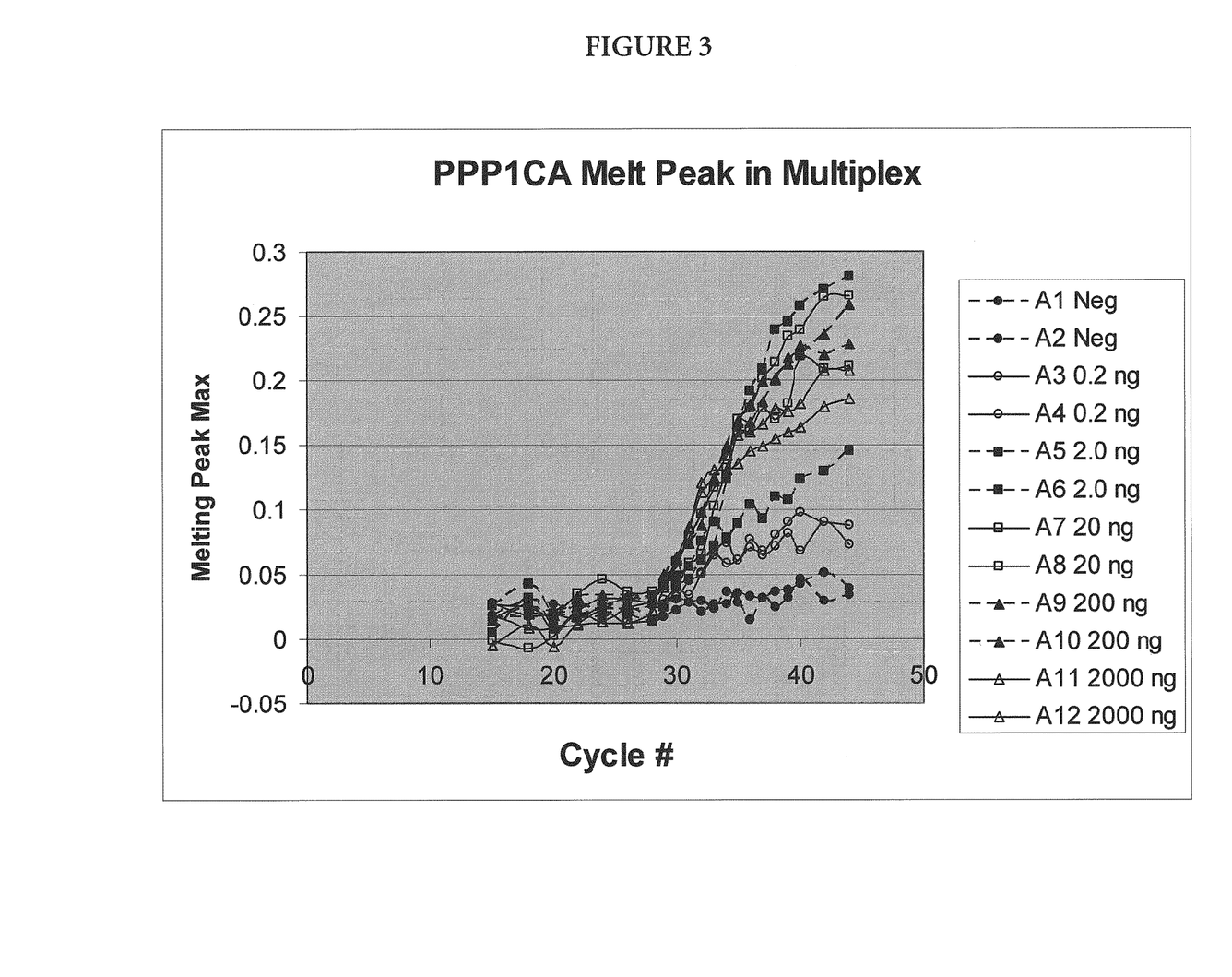
FIG. 3 shows the results of the method of the present invention as applied to the target nucleic acid sequence PPP1CA and described in Example 1.

As shown on FIGS. 2 and 3, for each amount of the target nucleic acid, the experiment was performed in duplicate. For each target, all twelve reactions (including two no-template control reactions) utilized the same fluorescently labeled probe.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method for amplification, detection and quantification of one or more target nucleic acids in a single sample container comprising the steps of:
    (a) contacting a sample, suspected of containing one or more target nucleic acids, with at least one set of oligonucleotides, each oligonucleotide within the set labeled with the same one or more reporter moieties, wherein each said labeled oligonucleotide
        i. is sufficiently complementary to at least a subsequence of at least one target nucleic acid;
        ii. is capable of binding to the corresponding target nucleic acid with a melting temperature distinct from the melting temperatures of the other labeled oligonucleotides within the same set;
    (b) amplifying the target nucleic acids in the sample in an amplification reaction that includes a temperature change interval, wherein said labeled oligonucleotides bound to corresponding target nucleic acids dissociate from the corresponding target nucleic acids;
    (c) detecting light emission from said reporter moieties over at least a portion of said temperature change interval; and
    (d) plotting the first derivative of said light emission detected in step (c) over at least said portion of the temperature change interval;
    (e) determining the maximum value of said derivative plotted in step (d);
    (f) repeating steps (b) through (e) multiple times; and
    (g) plotting the maximum values of said derivative determined in step (e) against the number or repetitions of steps (b) through (e), and determining the number of repetitions at which a predetermined threshold value of the value determined in step (e) is reached, thus quantifying the relative amount of said target nucleic acid.

2. The method of claim 1, wherein a control nucleic acid of known concentration is subjected to the steps (a)-(f) simultaneously with said target nucleic acids and the value determined in step (f) for each target nucleic acid is compared to the value determined in step (f) for the control nucleic acid, thereby determining the absolute amount of each said target nucleic acid.

3. The method of claim 1, wherein each said oligonucleotide in step (a) is labeled with a single reporter moiety.

4. The method of claim 3, wherein said reporter moiety is fluorescent.

5. The method of claim 1, wherein each said oligonucleotide in step (a) is labeled with a reporter moiety and a quencher moiety.

6. The method of claim 5, wherein said reporter moiety and said quencher moiety are fluorophores.

7. The method of claim 5, wherein said reporter moiety is a fluorophore and said quencher moiety is a dark quencher.

8. The method of claim 5, wherein said reporter and quencher moiety are separated by a nuclease cleavage site.

* * * * *

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagcttcaaa tacacaatct gaaggatca                                       29

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcctggaag aaagtagaac tggga                                           25

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gactctgtga ttttactgaa agtgaaagat tcccagactc c                         41

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
-continued

<222> LOCATION: (26)..(26)
<223> OTHER INFORMATION: tert-butyl-benzyl-dA

<400> SEQUENCE: 4
aaccgcatat atggtttcta cgatga                                            26

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: tert-butyl-benzyl-dA

<400> SEQUENCE: 5
cgatgagtgc aagagacgct acaa                                              24

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
actgtggaaa acctt                                                        15
```